(12) United States Patent
Shu et al.

(10) Patent No.: US 12,279,875 B2
(45) Date of Patent: Apr. 22, 2025

(54) ELECTROCARDIOGRAM (ECG) SIGNAL DETECTION AND POSITIONING METHOD BASED ON WEAKLY SUPERVISED LEARNING

(71) Applicants: Qilu University of Technology (Shandong Academy of Sciences), Jinan (CN); SHANDONG COMPUTER SCIENCE CENTER (NATIONAL SUPERCOMPUTING CENTER IN JINAN), Jinan (CN)

(72) Inventors: Minglei Shu, Jinan (CN); Pengyao Xu, Jinan (CN); Shuwang Zhou, Jinan (CN); Zhaoyang Liu, Jinan (CN); Kaiwei Li, Jinan (CN)

(73) Assignees: QILU UNIVERSITY OF TECHNOLOGY (SHANDONG ACADEMY OF SCIENCES), Jinan (CN); SHANDONG COMPUTER SCIENCE CENTER (NATIONAL SUPERCOMPUTING CENTER IN JINAN), Jinan (CN)

( * ) Notice: Subject to any disclaimer, the term of this patent is extended or adjusted under 35 U.S.C. 154(b) by 0 days.

(21) Appl. No.: 18/539,331

(22) Filed: Dec. 14, 2023

(65) Prior Publication Data
US 2024/0350066 A1 Oct. 24, 2024

(30) Foreign Application Priority Data
Apr. 23, 2023 (CN) .......................... 2023104375867

(51) Int. Cl.
*A61B 5/318* (2021.01)
*A61B 5/00* (2006.01)
(Continued)

(52) U.S. Cl.
CPC .............. *A61B 5/318* (2021.01); *A61B 5/308* (2021.01); *A61B 5/7203* (2013.01); *G06N 3/0895* (2023.01)

(58) Field of Classification Search
CPC ....... A61B 5/308; A61B 5/318; A61B 5/7203; A61B 5/7267; G06N 3/045; G06N 3/048; G06N 3/0895; Y02A 90/10
See application file for complete search history.

(56) References Cited

U.S. PATENT DOCUMENTS

| | | | |
|---|---|---|---|
| 2021/0232813 A1 | 7/2021 | Huang et al. | |
| 2022/0391635 A1 | 12/2022 | Lian et al. | |
| 2024/0099656 A1* | 3/2024 | Cull | ..................... A61B 5/4266 |

FOREIGN PATENT DOCUMENTS

| | | |
|---|---|---|
| CN | 109602415 A | 4/2019 |
| CN | 111523502 A | 8/2020 |

(Continued)

OTHER PUBLICATIONS

Chen Pengyu, et al., Multi-scale feature fusion method for bundled tobacco leaf classification based on fine-grained classification network, Journal of Anhui Agricultural University, 2022, pp. 1013-1021, vol. 49, No. 6.

*Primary Examiner* — George Manuel
(74) *Attorney, Agent, or Firm* — Bayramoglu Law Offices LLC (57) ABSTRACT

An electrocardiograph (ECG) signal detection and positioning method based on weakly supervised learning is provided. A deep learning model mainly includes a multi-scale feature extraction module, a self-attention encoding module, and a classification and positioning module. An extracted original ECG signal is denoised and segmented to obtain a fixed-length pure ECG signal segment. In the convolutionally-connected multi-scale feature extraction module, a channel local attention (CLA) layer is introduced, and a
(Continued)

PReLU activation function is used to achieve a better local information extraction capability. The self-attention encoding module is introduced to establish an association between a local feature and a global feature. The classification and positioning module is introduced to output a general location of an abnormal signal. A fusion module enables the model to map a local predicted value onto a global predicted value, and model parameters are trained on a weakly annotated dataset.

6 Claims, 6 Drawing Sheets

(51) Int. Cl.
*A61B 5/308* (2021.01)
*G06N 3/0895* (2023.01)

(56) References Cited

FOREIGN PATENT DOCUMENTS

| CN | 112883803 A | 6/2021 |
| CN | 113361606 A | 9/2021 |
| CN | 113384277 A | 9/2021 |
| CN | 114912532 A | 8/2022 |
| CN | 115470827 A | 12/2022 |
| CN | 115470828 A | 12/2022 |
| CN | 115530788 A | 12/2022 |
| CN | 115581464 A | 1/2023 |
| CN | 115666387 A | 1/2023 |
| CN | 115985505 A | 4/2023 |

* cited by examiner

ELECTROCARDIOGRAM (ECG) SIGNAL DETECTION AND POSITIONING METHOD BASED ON WEAKLY SUPERVISED LEARNING

CROSS-REFERENCE TO THE RELATED APPLICATIONS

This application is based upon and claims priority to Chinese Patent Application No. 202310437586.7, filed on Apr. 23, 2023, the entire contents of which are incorporated herein by reference.

TECHNICAL FIELD

The present disclosure relates to the technical field of electrocardiograph (ECG) signal processing, and specifically to an ECG signal detection and positioning method based on weakly supervised learning.

BACKGROUND

As an important physiological signal, an ECG signal can well reflect the activity state of the heart. A normal ECG signal is in a specific pattern and can be well recognized, while an abnormal ECG signal often only undergoes a subtle change and is not easily recognized. With the vigorous development of neural network models, although ECG anomaly detection algorithms based on convolutional and recurrent neural networks have achieved good results, these algorithms rely on accurately annotated ECG signal data. As a result, the overall technical cost increases, and a classification result obtained cannot well explain a reason for discriminative classification.

SUMMARY

In order to overcome the shortcomings in the above technologies, the present disclosure provides an ECG signal detection and positioning method based on weakly supervised learning, which has high overall accuracy and does not need large-scale accurately-annotated data.

The technical solutions used in the present disclosure to resolve the technical problem thereof are as follows:

An ECG signal detection and positioning method based on weakly supervised learning includes the following steps:
a) collecting n pieces of ECG signal data of different lengths from a plurality of collection devices to obtain an original ECG dataset $X_0$, where $X_0 = \{x_1, x_2, \ldots, x_j, \ldots, x_n\}$, $x_j$ represents a $j^{th}$ original ECG signal record, and $j \in \{1, 2, \ldots, n\}$;
b) preprocessing the original ECG dataset $X_0$ to obtain a preprocessed ECG dataset $X_0'$, where $X_0' = \{x_1', x_2', \ldots, x_j', \ldots, x_n'\}$, and $x_j'$ represents a $j^{th}$ preprocessed original ECG signal record;
c) establishing a deep learning model, and inputting the preprocessed ECG dataset into the deep learning model to obtain a globally recorded category prediction value $y^{pre}$ and a predicted abnormal signal location set L; and
d) training the deep learning model.

Further, the step b) includes the following substeps:
b-1) removing noise of another wave band from the original ECG dataset $X_0$ by using a bandpass filter; and
b-2) slicing the original ECG dataset $X_0$ without the noise of the another wave band into fixed-length signals by using a sliding window, to obtain the preprocessed ECG dataset $X_0'$.

Preferably, in the step b-1), the noise of the another wave band is removed by using a 3-45 Hz bandpass filter.

Further, the step c) includes the following substeps:
c-1) constituting the deep learning model by a multi-scale feature extraction module, a self-attention encoding module, and a classification and positioning module;
c-2) constituting the multi-scale feature extraction module of the deep learning model by a start convolutional block, a first multi-scale feature extraction block, and a second multi-scale feature extraction block, where the start convolutional block of the multi-scale feature extraction module is sequentially constituted by a first start convolutional layer, a batch normalization (BN) layer, a PReLU activation function layer, and a second start convolutional layer; and inputting the $j^{th}$ preprocessed original ECG signal record $x_j'$ into the start convolutional block of the multi-scale feature extraction module to obtain a feature map $X_1$;
c-3) constituting the first multi-scale feature extraction block of the multi-scale feature extraction module by a first BN layer, a first PReLU activation function layer, a channel local attention (CLA) layer, a first convolutional layer, a second BN layer, a second PReLU activation function layer, a dropout layer, a second convolutional layer, and a maximum pooling layer, where the CLA layer is constituted by a first branch and a second branch, the first branch of the CLA layer is sequentially constituted by a global average pooling layer, a first fully connected layer, a Swish activation function layer, a second fully connected layer, and a Sigmoid activation function layer, and the second branch of the CLA layer is sequentially constituted by a global maximum pooling layer, a maximum pooling layer, a first fully connected layer, a Swish activation function layer, a second fully connected layer, a Sigmoid activation function layer, and an upsampling layer; sequentially inputting the feature map $X_1$ into the first BN layer and the first PReLU activation function layer of the first multi-scale feature extraction block to obtain a feature map $X_{1\_1}$; inputting the feature map $X_{1\_1}$ into the first branch of the CLA layer of the first multi-scale feature extraction block to obtain a feature map $X_{1\_1}^{1\_2}$; inputting the feature map $X_{1\_1}$ into the second branch of the CLA layer of the first multi-scale feature extraction block to obtain a feature map $X_{1\_1}^{2\_3}$; multiplying the feature map $X_{1\_1}$ and the feature map $X_{1\_1}^{1\_2}$, and then multiplying a product and the feature map $X_{1\_1}^{2\_3}$ to obtain a feature map $X_{1\_2}$; sequentially inputting the feature map $X_{1\_2}$ into the first convolutional layer, the second BN layer, the second PReLU activation function layer, the dropout layer, and the second convolutional layer of the first multi-scale feature extraction block to obtain a feature map $X_{1\_3}$; and adding up the feature map $X_{1\_3}$ and the feature map $X_1$, and then inputting an addition result into the maximum pooling layer of the first multi-scale feature extraction block to obtain a feature map $X_2$;
c-4) constituting the second multi-scale feature extraction block of the multi-scale feature extraction module by a first BN layer, a first PReLU activation function layer, a CLA layer, a first convolutional layer, a second BN layer, a second PReLU activation function layer, a dropout layer, a second convolutional layer, and a maximum pooling layer; sequentially inputting the feature map $X_2$ into the first BN layer and the first PReLU activation function layer of the second multi-scale feature extraction block to obtain a feature map $X_{2\_1}$; inputting the feature map $X_{2\_1}$ into a first branch of the CLA layer of the second multi-scale feature extraction block to obtain a feature map $X_{2\_1}^{1-2}$; inputting the feature map $X_{2\_1}$ into a second branch of the CLA layer of the second multi-scale feature extraction block to obtain a feature map $X_{2\_1}^{2-3}$; multiplying the feature map $X_{2\_1}$ and the feature map $X_{2\_1}^{1-2}$, and then multiplying a product and the feature map $X_{2\_1}$ to obtain a feature map $X_{2\_2}$; sequentially inputting the feature map $X_{2\_2}$ into the first convolutional layer, the second BN layer, the second PReLU activation function layer, the dropout layer, and the second convolutional layer of the second multi-scale feature extraction block to obtain a feature map $X_{2\_3}$; and adding up the feature map $X_{2\_3}$ and the feature map $X_2$, and then inputting an addition result into the maximum pooling layer of the second multi-scale feature extraction block to obtain a feature map $X_3$;

c-5) encoding the feature map $X_3$ based on a predefined location to obtain a location information graph $X_3^P$, and concatenating the feature map $X_3$ and the location information graph $X_3^P$ to obtain a feature map $X_4$;

c-6) constituting the self-attention encoding module of the deep learning model by a multi-head self-attention layer, a layer norm layer, and a multi-layer perceptron (MLP) layer, and inputting the feature map $X_4$ into the self-attention encoding module to obtain a feature map $X_5$;

c-7) constituting the classification and positioning module by a local classification module, a fusion module, and an abnormal location output module;

c-8) constituting the local classification module of the classification and positioning module sequentially by a convolutional layer, a flatten layer, a fully connected layer, and a Softmax function; and inputting the feature map $X_5$ into the local classification module to obtain a predicted value $y_c^{pre}$ of a local location, where $y_c^{pre} = \{y_1^{pre}, y_2^{pre}, \ldots, y_l^{pre}, \ldots y_c^{pre}\}$, $y_l^{pre}$ presents a value p by the fully connected layer for an $l^{th}$ location, $l \in \{1, 2, \ldots, m\}$, m represents a quantity of predicted values output by the fully connected layer, $y_l^{pre}=0$ indicates a normal ECG signal, and $y_l^{pre}=1$ indicates an abnormal ECG signal;

c-9) inputting the predicted value $y_c^{pre}$ of the local location into the fusion module of the classification and positioning module to obtain the globally recorded category prediction value $y^{pre}$; and c-10) inputting the predicted value $y_c^{pre}$ of the local location into the abnormal location output module of the classification and positioning module, such that the abnormal location output module determines whether each location in the predicted value y pre of the local location has an abnormal signal, and outputs the abnormal signal location set L, where $L=\{l_1, l_2, \ldots, l_i, \ldots, l_k\}$, $l_i$ represents coordinates of a location of an $i^{th}$ abnormal signal in the predicted value $y_c^{pre}$ of the local location, $i \in \{1, 2, \ldots, k\}$, and k represents a quantity of predicted abnormal signals.

Preferably, in the step c-2), the first start convolutional layer of the start convolutional block has a 1*1 convolution kernel, with a step of 1, and the second start convolutional layer has a 3*3 convolution kernel, with a step of 2; in the step c-3), the first convolutional layer and the second convolutional layer of the first multi-scale feature extraction block each are a one-dimensional convolution with an 8*8 convolution kernel, a parameter size of the dropout layer of the first multi-scale feature extraction block is 0.2, and the maximum pooling layer of the first multi-scale feature extraction block has a convolution kernel whose size is 2, with a step of 2; in the step c-3), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32; in the step c-4), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32; and in the step c-6), a multi-head self-attention in the MLP layer has 6 heads.

Further, in the step d), a deep learning module is optimized by using an Adam optimizer based on a cross-entropy loss function, to obtain a trained deep learning model.

Further, in the step c-9), the globally recorded category prediction value $y^{pre}$ is calculated according to a formula $y^{pre}=(1/b^2)\log((1/m)\Sigma_{l=1}^{exp}(by_l^{pre}))$, where b is a constant.

Preferably, and b=3.

The present disclosure has following beneficial effects: The present disclosure does not require large-scale accurately-annotated data, but only requires some coarsely-grained annotated data to train model parameters to obtain an overall classification algorithm model. The present disclosure is capable of processing long continuous ECG signals, suitable for demands of different collection devices. Moreover, the present disclosure can identify a category of a signal and a specific location of the signal within a signal segment, providing an interpretable basis for category classification, and achieves high overall accuracy.

DETAILED DESCRIPTION OF THE EMBODIMENTS

Figure 1:
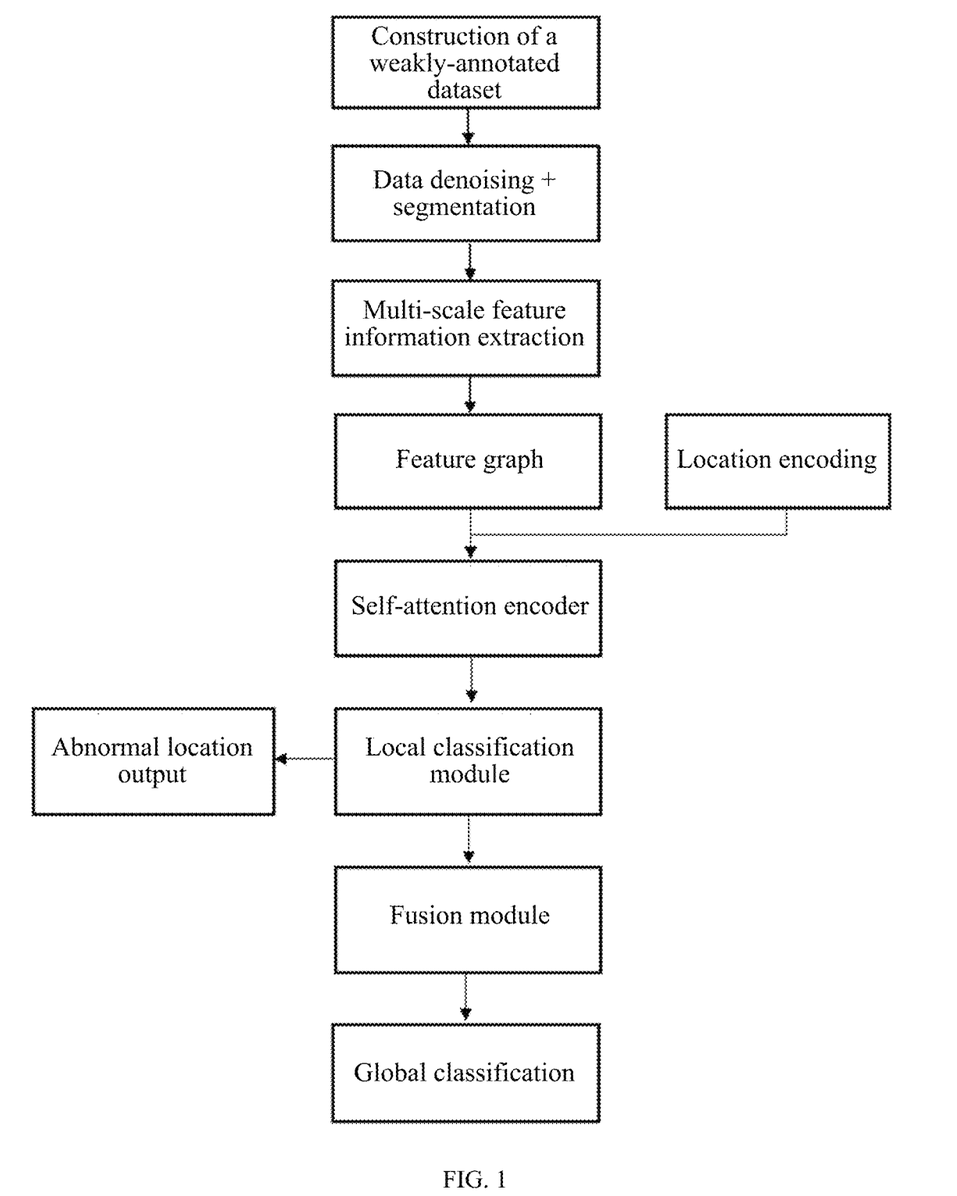
FIG. 1 is a flowchart of a method according to the present disclosure.
Figure 2:
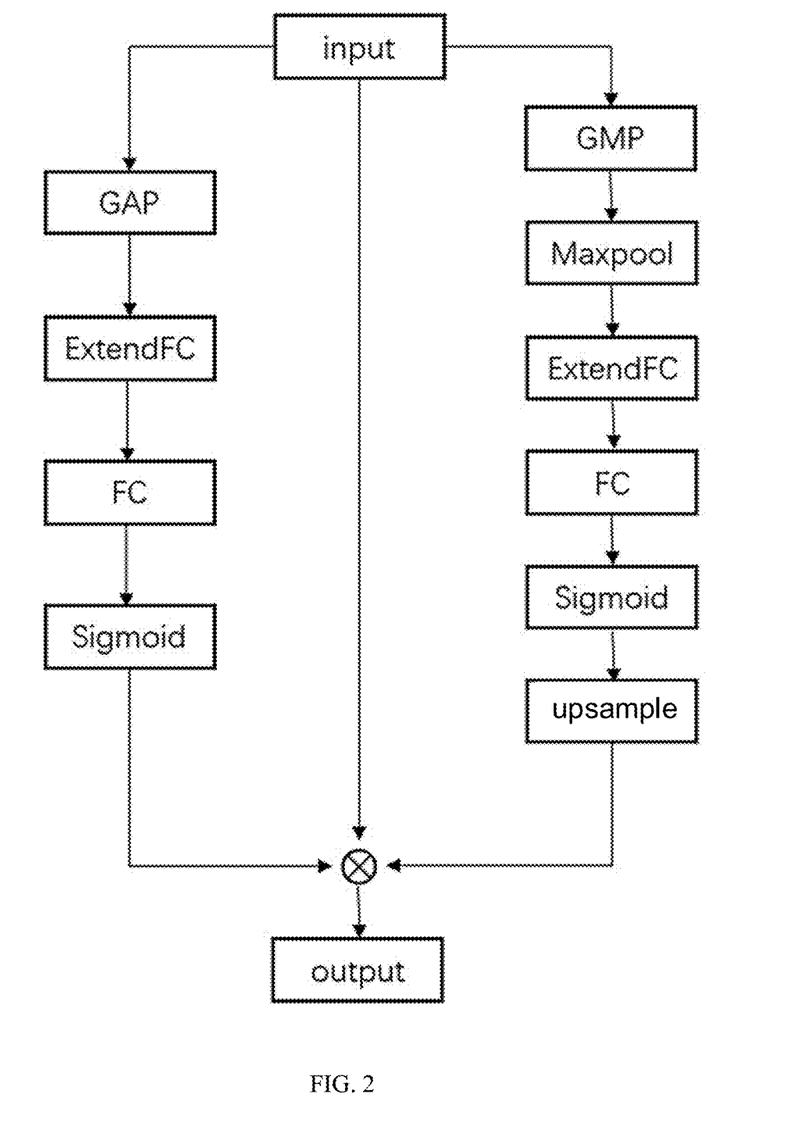
FIG. 2 is a structural diagram of a CLA model according to the present disclosure.

The present disclosure is further described with reference to FIG. 1 and FIG. 2.

An ECG signal detection and positioning method based on weakly supervised learning includes the following steps:

a) n pieces of ECG signal data of different lengths are collected from a plurality of collection devices to obtain original ECG dataset $X_0$, where $X_0=\{x_1, x_2, \ldots, x_j, \ldots, x_n\}$, $x_j$ represents a $j^{th}$ original ECG signal record, and $j \in \{1, 2, \ldots, n\}$.

b) The original ECG dataset $X_0$ is preprocessed to obtain preprocessed ECG dataset $X_0'$, where $X_0'=\{x_1', x_2', \ldots, x_j', \ldots, x_n'\}$, and $x_j'$ represents a $j^{th}$ preprocessed original ECG signal record.

c) A deep learning model is established, and the preprocessed ECG dataset is input into the deep learning model to obtain globally recorded category prediction value $y^{pre}$ and predicted abnormal signal location set L. The deep learning model is constituted by a multi-scale feature extraction module, a self-attention encoding module, and a classification and positioning module. The multi-scale feature extraction module uses convolutional kernels of different sizes to extract different information, integrates local information, and makes an extracted feature map contain more original information. The self-attention encoding module uses an attention mechanism to partially associate the local information with a global feature to better recognize an overall category. The classification and positioning module of the model outputs one-dimensional location coordinates of an abnormal signal in a signal record.

d) The deep learning model is trained. After a plurality of rounds of iterative optimization, an optimized deep learning model is obtained. Finally, a model capable of processing long continuous ECG signals is obtained to determine whether an input signal is an abnormal signal and location coordinates of the input signal in an abnormal segment.

The deep learning model mainly includes the multi-scale feature extraction module, the self-attention encoding module, and a classification and positioning module. An extracted original ECG signal is denoised and segmented to obtain a fixed-length pure ECG signal segment, which meets an input requirement of a network model in the present disclosure. In the convolutionally-connected multi-scale feature extraction module, a CLAayer is introduced, and a PReLU activation function is used to achieve a better local information extraction capability. The self-attention encoding module is introduced to establish an association between a local feature and a global feature to enhance a recognition capability of an important feature. The classification and positioning module is introduced to output a general location of the abnormal signal to improve interpretability of category classification. A fusion module enables the model to map a local predicted value onto a global predicted value, and model parameters are trained on a weakly annotated dataset, thereby greatly reducing a cost of technical implementation.

Embodiment 1

The step b) includes the following substeps:

b-1) Noise of another wave band is removed from the original ECG dataset $X_0$ by using a bandpass filter, to meet a demand for processing ECG signals of different lengths. In an embodiment of the present disclosure, preferably, in the step b-1), the noise of the another wave band is removed by using a 3-45 Hz bandpass filter.

b-2) The original ECG dataset $X_0$ without the noise of the another wave band is sliced into fixed-length signals by using a sliding window, to obtain the preprocessed ECG dataset $X_0'$.

Embodiment 2

The step c) includes the following substeps:

c-1) The deep learning model is constituted by the multi-scale feature extraction module, the self-attention encoding module, and the classification and positioning module.

c-2) The multi-scale feature extraction module of the deep learning model is constituted by a start convolutional block, a first multi-scale feature extraction block (MFE block), and a second multi-scale feature extraction block (MFE block). The start convolutional block of the multi-scale feature extraction module is sequentially constituted by a first start convolutional layer, a BN layer, a PReLU activation function layer, and a second start convolutional layer. The $j^{th}$ preprocessed original ECG signal record $x_j'$ is input into the start convolutional block of the multi-scale feature extraction module to obtain feature map $X_1$.

c-3) The first multi-scale feature extraction block of the multi-scale feature extraction module is constituted by a first BN layer, a first PReLU activation function layer, a CLA layer, a first convolutional layer, a second BN layer, a second PReLU activation function layer, a dropout layer, a second convolutional layer, and a maximum pooling layer. The CLA layer is constituted by a first branch and a second branch. The first branch of the CLA layer is sequentially constituted by a global average pooling layer, a first fully connected layer, a Swish activation function layer, a second fully connected layer, and a Sigmoid activation function layer. The second branch of the CLA layer is sequentially constituted by a global maximum pooling layer, a maximum pooling layer, a first fully connected layer, a Swish activation function layer, a second fully connected layer, a Sigmoid activation function layer, and an upsampling layer. The feature map $X_1$ is sequentially into the first BN layer and the first PReLU activation function layer of the first multi-scale feature extraction block to obtain feature map $X_{1\_1}$. The feature map $X_{1\_1}$ is input into the first branch of the CLA layer of the first multi-scale feature extraction block to obtain feature map $X_{1\_1}^{1-2}$. The feature map $X_{1\_1}$ is input into the second branch of the CLA layer of the first multi-scale feature extraction block to obtain feature map $X_{2\_1}^{2-3}$. The feature map $X_{1\_1}$ and the feature map $X_{1\_1}^{1-2}$ are multiplied, and then a product and the feature map $X_{1\_1}^{2-3}$ are multiplied to obtain feature map $X_{1\_2}$. The feature map $X_{1\_2}$ is sequentially input into the first convolutional layer, the second BN layer, the second PReLU activation function layer, the dropout layer, and the second convolutional layer of the first multi-scale feature extraction block to obtain feature map $X_{1\_3}$. The feature map $X_{1\_3}$ and the feature map $X_1$ are added up, and an addition result is input into the maximum pooling layer of the first multi-scale feature extraction block to obtain feature map $X_2$.

c-4) The second multi-scale feature extraction block of the multi-scale feature extraction module is constituted by a first BN layer, a first PReLU activation function layer, a CLA layer, a first convolutional layer, a second BN layer, a second PReLU activation function layer, a dropout layer, a second convolutional layer, and a maximum pooling layer. The feature map $X_2$ is sequentially input into the first BN layer and the first PReLU activation function layer of the second multi-scale feature extraction block to obtain feature map $X_{2\_1}$. The feature map $X_{2\_1}$ is input into a first branch of the CLA layer of the second multi-scale feature extraction block to obtain feature map $X_{2\_1}^{1-2}$. The feature map $X_{2\_1}$ is input into a second branch of the CLA layer of the second multi-scale feature extraction block to obtain feature map $X_{2\_1}^{2-3}$. The feature map $X_{2\_1}$ and the feature map $X_{2\_1}^{1-2}$ are multiplied, and then a product and the feature map $X_{2\_1}^{2-3}$ are multiplied to obtain feature map $X_{2\_2}$. The feature map $X_{2\_2}$ is sequentially input into the first convolutional layer, the second BN layer, the second PReLU activation function layer, the dropout layer, and the second convolutional layer of the second multi-scale feature extraction block to obtain feature map $X_{2\_3}$. The feature map $X_{2\_3}$ and the feature map $X_2$ are added up, and then an addition result is input into the maximum pooling layer of the second multi-scale feature extraction block to obtain feature map $X_3$.

c-5) The feature map $X_3$ is encoded based on a predefined location to obtain location information graph $X_3^P$, and the feature map $X_3$ and the location information graph $X_3^P$ are concatenated to obtain feature map $X_4$.

c-6) The self-attention encoding module of the deep learning model is constituted by a multi-head self-attention layer, a layer norm layer, and an MLP layer, and the feature map $X_4$ is input into the self-attention encoding module to obtain feature map $X_5$. The attention encoding module can obtain a feature map atlas of a correlation between a local feature and a global information feature.

c-7) The classification and positioning module is constituted by a local classification module, a fusion module, and an abnormal location output module. The fusion module maps a local predicted value onto a global prediction. The abnormal location output module outputs a location of an abnormal signal segment by determining a local category.

c-8) The local classification module of the classification and positioning module is constituted sequentially by a convolutional layer, a flatten layer, a fully connected layer, and a Softmax function. The feature map $X_5$ is input into the local classification module to obtain predicted value $y_c^{pre}$ of a local location, where $y_c^{pre} = \{y_1^{pre}, y_2^{pre}, \ldots, y_l^{pre}, \ldots, y_m^{pre}\}$, $y_l^{pre}$ presents a value p by the fully connected layer for an $l^{th}$ location, $l \in \{1, 2, \ldots, m\}$, m represents a quantity of predicted values output by the fully connected layer, $y_l^{pre}=0$ indicates a normal ECG signal, and $y_l^{pre}=1$ indicates an abnormal ECG signal.

c-9) The predicted value $y_c^{pre}$ of the local location is input into the fusion module of the classification and positioning module to obtain the globally recorded category prediction value $y^{pre}$.

c-10) The predicted value $y_c^{pre}$ of the local location is input into the abnormal location output module of the classification and positioning module, such that the abnormal location output module determines whether each location in the predicted value $y_c^{pre}$ of the local location has an abnormal signal, and outputs the abnormal signal location set L, where $L=\{l_1, l_2, \ldots, l_i, \ldots, l_k\}$, $l_i$ represents coordinates of a location of an $i^{th}$ abnormal signal in the predicted value $y_c^{pre}$ of the local location, $i \in \{1, 2, \ldots, k\}$, and k represents a quantity of predicted abnormal signals. A value of k is changeable. This is because some records have abnormal signals, but some records have no abnormal signal, and a quantity of predicted abnormal signals in each record is uncertain.

In an embodiment of the present disclosure, in the step c-2), the first start convolutional layer of the start convolutional block has a 1*1 convolution kernel, with a step of 1, and the second start convolutional layer has a 3*3 convolution kernel, with a step of 2. In the step c-3), the first convolutional layer and the second convolutional layer of the first multi-scale feature extraction block each are a one-dimensional convolution with an 8*8 convolution kernel, a parameter size of the dropout layer of the first multi-scale feature extraction block is 0.2, and the maximum pooling layer of the first multi-scale feature extraction block has a convolution kernel whose size is 2, with a step of 2. In the step c-3), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32. In the step c-4), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32. In the step c-6), a multi-head self-attention in the MLP layer has 6 heads.

Embodiment 3

In the step d), a deep learning module is optimized by using an Adam optimizer based on a cross-entropy loss function, to obtain a trained deep learning model. During the training, parameters of the model are optimized by using the Adam optimizer. After a plurality of rounds of iterative optimization, a model capable of processing long continuous ECG signals is finally obtained to determine whether an input signal is an abnormal signal and location coordinates of the input signal in an abnormal segment.

Embodiment 4

In the step c-9), the globally recorded category prediction value y pre is calculated according to formula $y^{pre}=(1/b^2) \log((1/m)\Sigma_{i=1}^m \exp(by_i^{pre}))$, where b is a constant. In an embodiment of the present disclosure, b=3.

Finally, it should be noted that the above descriptions are only preferred embodiments of the present disclosure, and are not intended to limit the present disclosure. Although the present disclosure has been described in detail with reference to the foregoing embodiments, those skilled in the art may still modify the technical solutions described in the foregoing embodiments, or equivalently substitute some technical features thereof. Any modification, equivalent substitution, improvement, etc. within the spirit and principles of the present disclosure shall fall within the scope of protection of the present disclosure.

In order to verify reliability of the patented method, local predicted value $y_c^{pre}$ is selected for systematic evaluation to achieve three-way classification for signal $X_j$ in our experiment. Herein, N1, N2, and N3 are used to represent category names of classifying the $y_c^{pre}$.

TABLE 1

Comparison of different experimental methods

| Method | N1 | | | N2 | | | N3 | | |
|---|---|---|---|---|---|---|---|---|---|
| | Ppr | Se | F1 | Ppr | Se | F1 | Ppr | Se | F1 |
| SVM | 0.980 | 0.940 | 0.959 | 0.620 | 0.530 | 0.571 | 0.594 | 0.873 | 0.707 |
| SRT | 0.994 | 0.909 | 0.950 | 0.488 | 0.808 | 0.608 | 0.8254 | 0.822 | 0.838 |
| CNN-WSL | 0.978 | 0.986 | 0.982 | 0.623 | 0.747 | 0.679 | 0.9467 | 0.7437 | 0.833 |
| Resnet | 0.958 | 0.815 | 0.881 | 0.400 | 0.284 | 0.333 | 0.244 | 0.782 | 0.372 |
| our | 0.993 | 0.976 | 0.984 | 0.687 | 0.828 | 0.751 | 0.847 | 0.954 | 0.897 |

Figure 3:
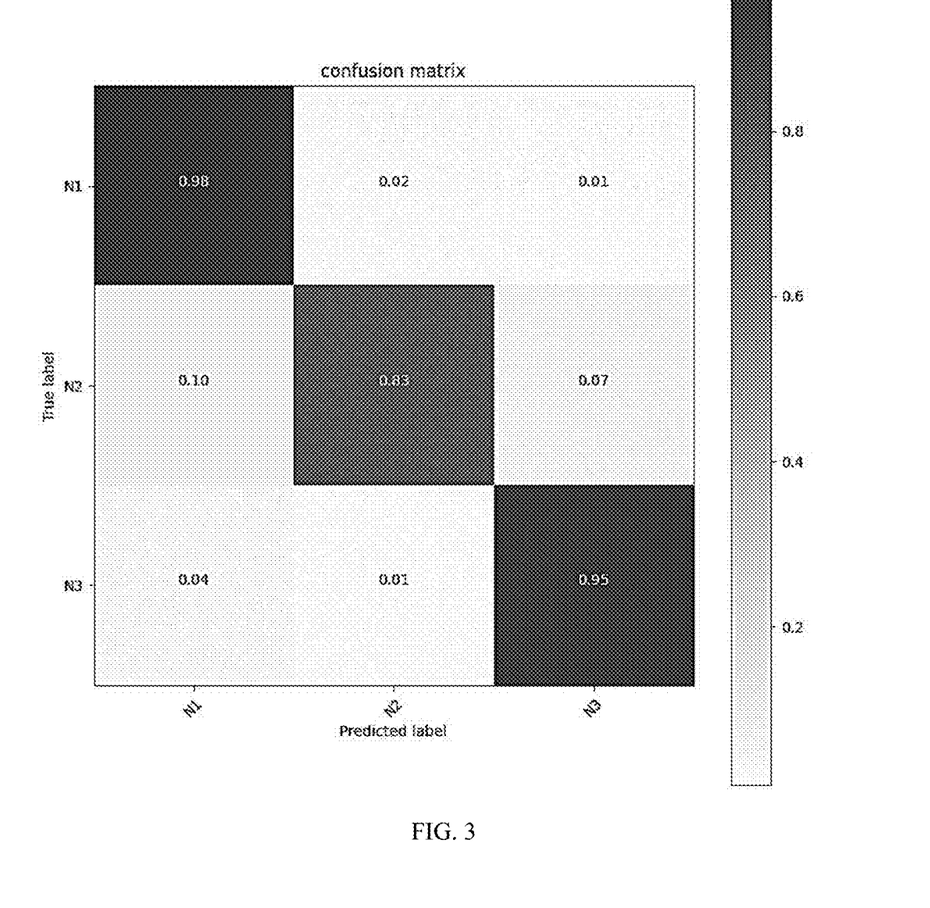
FIG. 3 shows our method.
Figure 4:
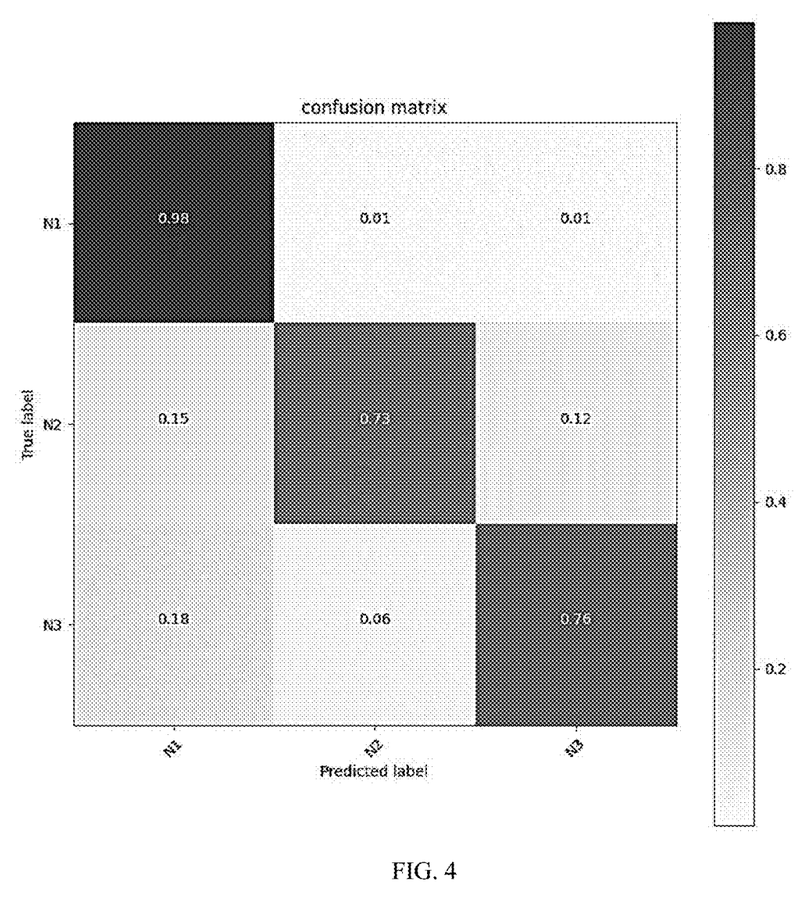
FIG. 4 shows Resnet18.
Figure 5:
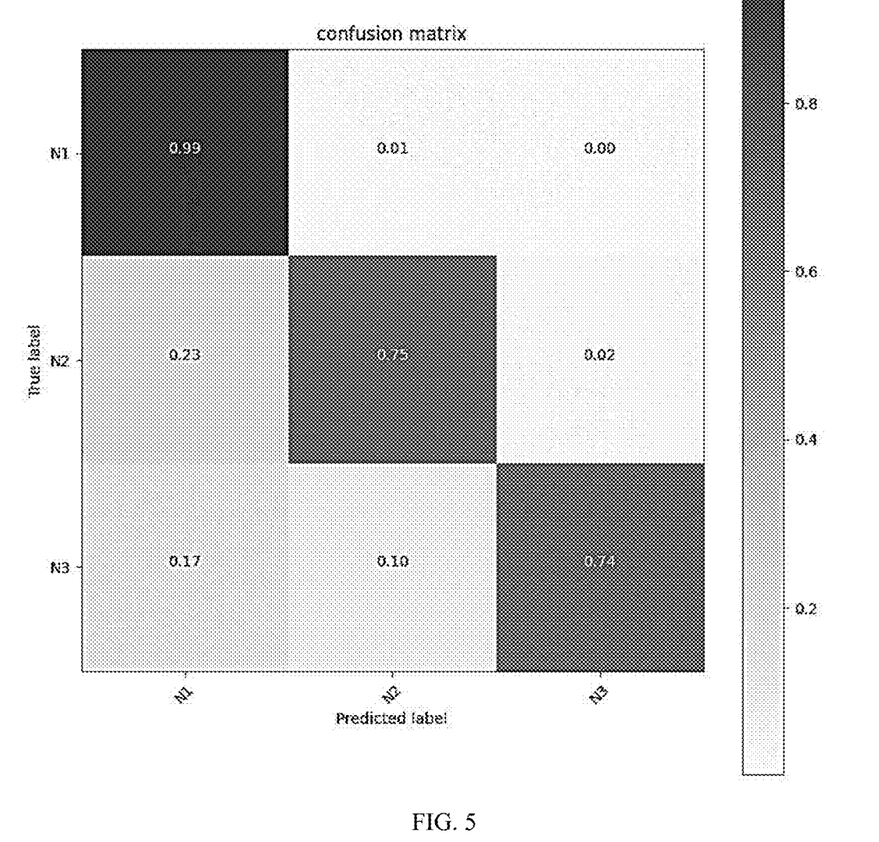
FIG. 5 shows CNN+WSL method.

Our experimental method is compared with two traditional deep learning methods SVM and resnet, as well as the methods SRT and CNN-WSL proposed in relevant papers. According to our method, three-way classification of a data signal is achieved, with evaluation indicators sensitivity (Ppr), specificity (se), and F1. In the experiment, indicator parameters of each category are calculated to better demonstrate classification performance of our method. From the data in the table, it can be seen that performance of the method in the present disclosure is optimal in the categories N1 and N2, and has a significant performance improvement in the category N2 compared with other methods. In addition, fusion matrices of different experimental methods in FIG. 3 to FIG. 5 are also compared, and it is found that compared with the benchmark model resnet18, an equal state is basically achieved in the category N, with a more significant improvement in the categories N2 and N3.

For the category N2, our method has an improvement of 8% compared with the previous methods. For the category N3, our method has an improvement of 19%. Due to imbalance of our training dataset, the category N3 accounts for one twentieth of the overall dataset. This performance improvement indicates that our method can achieve more fine-grained recognition and classification.

Figure 6:
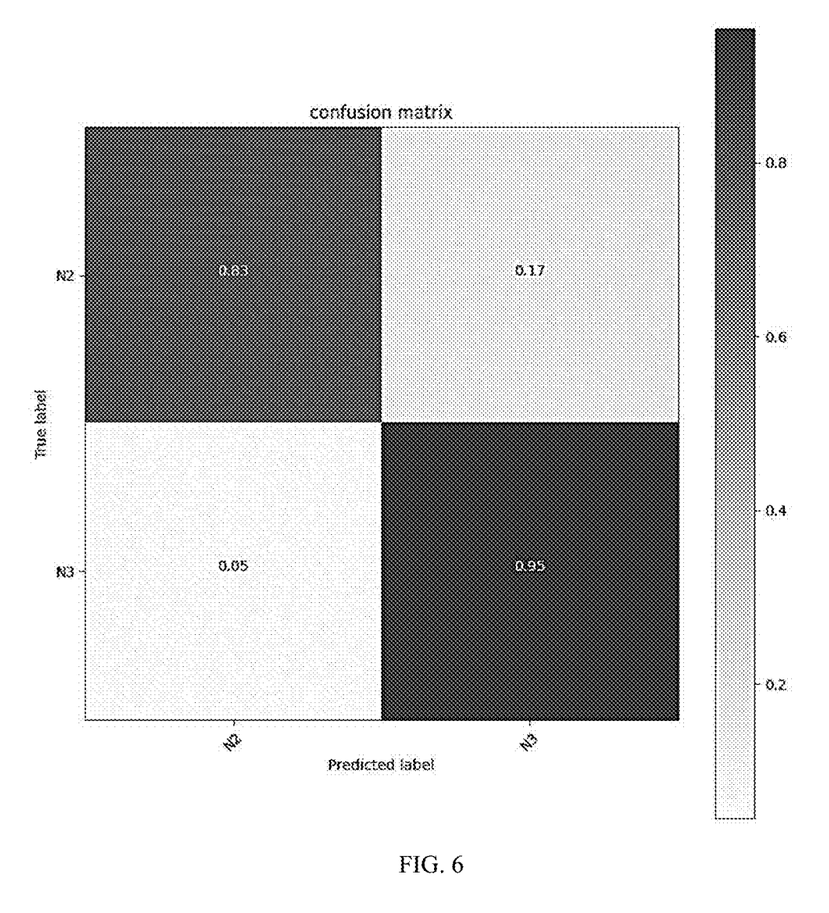
FIG. 6 shows a location fusion matrix.

In the experiment, the categories N2 and N3 are defined as abnormal signal categories. In FIG. 6, anomaly set L and correctness of locations of the categories N2 and N3 are analyzed. From the figure, it can be seen that recognition accuracy of the category N2 is 0.83, and recognition accuracy of the category N3 is 0.95, which are both high positioning accuracy.

What is claimed is:
1. An electrocardiograph (ECG) detection and positioning method based on weakly supervised learning, comprising the following steps:
   a-1) operating a plurality of ECG devices to obtain n pieces of ECG signal data of different lengths;
   a-2) collecting the n pieces of ECG signal data of different lengths from the plurality of ECG devices to obtain an original ECG dataset $X_0$, wherein $X_0 = \{x_1, x_2, \ldots, x_j, \ldots, x_n\}$, $x_j$ represents a $j^{th}$ original ECG signal record, and $j \in \{1, 2, \ldots, n\}$;
   b) preprocessing the original ECG dataset $X_0$ to obtain a preprocessed ECG dataset $X_0'$, wherein $X_0' = \{x_1', x_2', \ldots, x_j', \ldots, x_n'\}$, and $x_j'$ represents a $j^{th}$ preprocessed original ECG signal record;
   c) establishing a deep learning model, and inputting the preprocessed ECG dataset into the deep learning model to obtain a globally recorded category prediction value $y^{pre}$ and a predicted abnormal signal location set L; and
   d) training the deep learning model;

wherein the step c) comprises the following substeps:
   c-1) constituting the deep learning model by a multi-scale feature extraction module, a self-attention encoding module, and a classification and positioning module;
   c-2) constituting the multi-scale feature extraction module of the deep learning model by a start convolutional block, a first multi-scale feature extraction block, and a second multi-scale feature extraction block, wherein the start convolutional block of the multi-scale feature extraction module is sequentially constituted by a first start convolutional layer, a batch normalization (BN) layer, a PRELU activation function layer, and a second start convolutional layer; and inputting the $j^{th}$ preprocessed original ECG signal record $x_j'$ into the start convolutional block of the multi-scale feature extraction module to obtain a feature map $X_1$;
   c-3) constituting the first multi-scale feature extraction block of the multi-scale feature extraction module by a first BN layer, a first PRELU activation function layer, a channel local attention (CLA) layer, a first convolutional layer, a second BN layer, a second PRELU activation function layer, a dropout layer, a second convolutional layer, and a maximum pooling layer, wherein the CLA layer is constituted by a first branch and a second branch, the first branch of the CLA layer is sequentially constituted by a global average pooling layer, a first fully connected layer, a Swish activation function layer, a second fully connected layer, and a Sigmoid activation function layer, and the second branch of the CLA layer is sequentially constituted by a global maximum pooling layer, a maximum pooling layer, a first fully connected layer, a Swish activation function layer, a second fully connected layer, a Sigmoid activation function layer, and an upsampling layer; sequentially inputting the feature map $X_1$ into the first BN layer and the first PRELU activation function layer of the first multi-scale feature extraction block to obtain a feature map $X_{1\_1}$; inputting the feature map $X_{1\_1}$ into the first branch of the CLA layer of the first multi-scale feature extraction block to obtain a feature map $X_{1\_1}^{1-2}$; inputting the feature map $X_{1\_1}$ into the second branch of the CLA layer of the first multi-scale feature extraction block to obtain a feature map $X_{1\_1}^{2-3}$; multiplying the feature map $X_{1\_1}$ and the feature map $X_{1\_1}^{1-2}$ to obtain a first product, and then multiplying the first product and the feature map $X_{1\_1}^{2-3}$ to obtain a feature map $X_{1\_2}$; sequentially inputting the feature map $X_{1\_2}$ into the first convolutional layer, the second BN layer, the second PRELU activation function layer, the dropout layer, and the second convolutional layer of the first multi-scale feature extraction block to obtain a feature map $X_{1\_3}$; and adding up the feature map $X_{1\_3}$ and the feature map $X_1$ to obtain a first addition result, and then inputting the first addition result into the maximum pooling layer of the first multi-scale feature extraction block to obtain a feature map $X_2$;

c-4) constituting the second multi-scale feature extraction block of the multi-scale feature extraction module by a first BN layer, a first PRELU activation function layer, a CLA layer, a first convolutional layer, a second BN layer, a second PRELU activation function layer, a dropout layer, a second convolutional layer, and a maximum pooling layer; sequentially inputting the feature map $X_2$ into the first BN layer and the first PRELU activation function layer of the second multi-scale feature extraction block to obtain a feature map $X_{2\_1}$; inputting the feature map $X_{2\_1}$ into a first branch of the CLA layer of the second multi-scale feature extraction block to obtain a feature map $X_{2\_1}^{1-2}$; inputting the feature map $X_{2\_1}$ into a second branch of the CLA layer of the second multi-scale feature extraction block to obtain a feature map $X_{2\_1}^{2-3}$; multiplying the feature map $X_{2\_1}$ and the feature map $X_{2\_1}^{1-2}$ to obtain a second product, and then multiplying the second product and the feature map $X_{2\_1}^{2-3}$ to obtain a feature map $X_{2\_2}$; sequentially inputting the feature map $X_{2\_2}$ into the first convolutional layer, the second BN layer, the second PRELU activation function layer, the dropout layer, and the second convolutional layer of the second multi-scale feature extraction block to obtain a feature map $X_{2\_3}$; and adding up the feature map $X_{2\_3}$ and the feature map $X_2$ to obtain a second addition result, and then inputting the second addition result into the maximum pooling layer of the second multi-scale feature extraction block to obtain a feature map $X_3$;

c-5) encoding the feature map $X_3$ based on a predefined location to obtain a location information graph $X_3^P$, and concatenating the feature map $X_3$ and the location information graph $X_3^P$ to obtain a feature map $X_4$;

c-6) constituting the self-attention encoding module of the deep learning model by a multi-head self-attention layer, a layer norm layer, and a multi-layer perceptron (MLP) layer, and inputting the feature map $X_4$ into the self-attention encoding module to obtain a feature map $X_5$;

c-7) constituting the classification and positioning module by a local classification module, a fusion module, and an abnormal location output module;

c-8) constituting the local classification module of the classification and positioning module sequentially by a convolutional layer, a flatten layer, a fully connected layer, and a Softmax function; and inputting the feature map $X_5$ into the local classification module to obtain a predicted value $y_c^{pre}$ of a local location, wherein $y_c^{pre} = \{y_1^{pre}, y_2^{pre}, \ldots, y_l^{pre}, \ldots y_m^{pre}\}$, $y_l^{pre}$ represents a predicted value output by the fully connected layer for an $l^{th}$ location, $l \in \{1, 2, \ldots, m\}$, m represents a pre quantity of predicted values output by the fully connected layer, $y_l^{pre}=0$ indicates a normal ECG signal, and $y_l^{pre}=1$ indicates an abnormal ECG signal;

c-9) inputting the predicted value $y_c^{pre}$ of the local location into the fusion module of the classification and positioning module to obtain the globally recorded category prediction value $y^{pre}$; and c-10) inputting the predicted value $y_c^{pre}$ of the local location into the abnormal location output module of the classification and positioning module, wherein the abnormal location output module determines whether each location in the predicted value $y_c^{pre}$ of the local location has an abnormal signal, wherein the abnormal signal reflects an activity state of a heart, and outputs the abnormal signal location set L, wherein $L=\{l, l_2, \ldots, l, \ldots, l_k\}$, $l_i$ represents coordinates of a location of an $i^{th}$ abnormal signal in the predicted value $y_c^{pre}$ of the local location, $i \in \{1, 2, \ldots, k\}$, and k represents a quantity of predicted abnormal signals;

wherein in the step c-9), the globally recorded category prediction value $y^{pre}$ is calculated according to a formula $y^{pre}=(1/b^2)\log((1/m)\Sigma_{l=1}^{m}\exp(by_l^{pre}))$, wherein b is a constant.

2. The ECG signal detection and positioning method based on weakly supervised learning according to claim 1, wherein the step b) comprises the following substeps:
   b-1) removing noise of another wave band from the original ECG dataset $X_0$ by using a bandpass filter; and
   b-2) slicing the original ECG dataset $X_0$ without the noise of the another wave band into fixed-length signals by using a sliding window, to obtain the preprocessed ECG dataset $X_0'$.

3. The ECG signal detection and positioning method based on weakly supervised learning according to claim 2, wherein in the step b-1), the noise of the another wave band is removed by using a 3-45 Hz bandpass filter.

4. The ECG signal detection and positioning method based on weakly supervised learning according to claim 1, wherein
   in the step c-2), the first start convolutional layer of the start convolutional block has a 1*1 convolution kernel, with a step of 1, and the second start convolutional layer has a 3*3 convolution kernel, with a step of 2;
   in the step c-3), the first convolutional layer and the second convolutional layer of the first multi-scale feature extraction block each are a one-dimensional convolution with an 8*8 convolution kernel, a parameter size of the dropout layer of the first multi-scale feature extraction block is 0.2, and the maximum pooling layer of the first multi-scale feature extraction block has a convolution kernel whose size is 2, with a step of 2;
   in the step c-3), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32;
   in the step c-4), an expansion coefficient of the first fully connected layer in the first branch of the CLA layer is 4, a parameter of the global maximum pooling layer in the second branch of the CLA layer is set to 1, the maximum pooling layer in the second branch of the CLA layer has a convolution kernel whose size is 32, with a step of 32, an expansion coefficient of the first fully connected layer in the second branch of the CLA layer is 4, and a parameter of the upsampling layer in the CLA layer is 32; and
   in the step c-6), a multi-head self-attention in the MLP layer has 6 heads.

5. The ECG signal detection and positioning method based on weakly supervised learning according to claim 1, wherein in the step d), a deep learning module is optimized by using an Adam optimizer based on a cross-entropy loss function, to obtain a trained deep learning model.

6. The ECG signal detection and positioning method based on weakly supervised learning according to claim 1, wherein b=3.

\* \* \* \* \*